United States Patent
Fischer et al.

(10) Patent No.: US 10,184,915 B2
(45) Date of Patent: Jan. 22, 2019

(54) INSPECTION PROBE

(71) Applicant: General Electric Technology GmbH, Baden (CH)

(72) Inventors: Reinhard Fischer, Zurich (CH); Andrew Lumley, Ultoxeter (GB); Dominik Loosli, Zurich (CH)

(73) Assignee: GENERAL ELECTRIC TECHNOLOGY GMBH, Baden (CH)

( * ) Notice: Subject to any disclaimer, the term of this patent is extended or adjusted under 35 U.S.C. 154(b) by 0 days.

(21) Appl. No.: 15/695,094

(22) Filed: Sep. 5, 2017

(65) Prior Publication Data
US 2018/0067084 A1 Mar. 8, 2018

(30) Foreign Application Priority Data

Sep. 6, 2016 (EP) .................................. 16187384

(51) Int. Cl.
*G01N 27/87* (2006.01)
*G01N 27/82* (2006.01)
(Continued)

(52) U.S. Cl.
CPC ...... *G01N 27/9046* (2013.01); *G01M 13/023* (2013.01); *G01N 27/87* (2013.01);
(Continued)

(58) Field of Classification Search
CPC ........... G01N 27/87; G01N 27/82; G01R 3/00
See application file for complete search history.

(56) References Cited

U.S. PATENT DOCUMENTS 5,372,147 A * 12/1994 Lathrop, Jr. ............ A61B 34/30
  128/898
5,411,043 A * 5/1995 Kamler ................... B08B 3/024
  122/392

(Continued)

FOREIGN PATENT DOCUMENTS

| DE | 102013106470 A1 | 12/2014 |
| EP | 1605259 A1 | 12/2005 |
| WO | 2014031957 A1 | 2/2014 |

OTHER PUBLICATIONS

European Search Report issued in connection with corresponding EP application 16187384.9 dated Feb. 27, 2017.

*Primary Examiner* — Lisa Caputo
*Assistant Examiner* — Jamel Williams
(74) *Attorney, Agent, or Firm* — GE Global Patent Operation; Rita D. Vacca

(57) ABSTRACT

An inspection apparatus, including an extendable structure, an inspection probe, a drive, a sensor, and a processor. The extendable structure includes an end fixed to the inspection probe and insertable into a gap defined between a first surface and a second surface. The extendable structure is configured to maintain physical contact with the first surface as the end transitions across the first surface. The drive is configured to position the inspection probe. The current sensor is coupled to the drive and configured to measure a drive load over a period of time the inspection probe transitions across the first surface. The processor is coupled to the sensor and is configured to receive a signal associated with the drive load corresponding to movement of the inspection probe, and determine an operating condition of the extendable structure based on the drive load signal.

15 Claims, 9 Drawing Sheets

(51) Int. Cl.
*G01R 3/00* (2006.01)
*G01N 27/90* (2006.01)
*G01M 13/02* (2006.01)
*G01R 31/00* (2006.01)

(52) U.S. Cl.
CPC .............. *G01R 3/00* (2013.01); *G01R 31/00* (2013.01); *G01N 27/9013* (2013.01); *G01N 2291/2693* (2013.01)

(56) References Cited

U.S. PATENT DOCUMENTS

| | | | | |
|---|---|---|---|---|
| 7,305,898 | B2 * | 12/2007 | Cabanis | G01N 27/9013 |
| | | | | 73/865.8 |
| 8,374,722 | B2 * | 2/2013 | Buckingham | B08B 9/045 |
| | | | | 104/138.2 |
| 9,261,489 | B2 * | 2/2016 | Jones | G01N 29/226 |
| 2002/0108644 | A1 * | 8/2002 | Hoadley | F23J 3/023 |
| | | | | 134/172 |
| 2003/0089183 | A1 * | 5/2003 | Jacobsen | G01N 29/045 |
| | | | | 73/865.8 |
| 2010/0251822 | A1 * | 10/2010 | Isobe | G01N 29/069 |
| | | | | 73/606 |
| 2013/0335530 | A1 * | 12/2013 | Hatcher, Jr. | G02B 23/2484 |
| | | | | 348/46 |
| 2013/0345894 | A1 * | 12/2013 | Haddad | G01N 35/1011 |
| | | | | 700/302 |
| 2014/0140800 | A1 * | 5/2014 | Inoue | B25J 9/042 |
| | | | | 414/744.5 |
| 2014/0310895 | A1 * | 10/2014 | Chen | H02P 29/00 |
| | | | | 15/21.1 |
| 2016/0363437 | A1 * | 12/2016 | Safai | G01N 21/954 |
| 2017/0361470 | A1 * | 12/2017 | Otero Del Real | B25J 18/02 |

* cited by examiner

INSPECTION PROBE

BACKGROUND

The field of the disclosure relates generally to a device for use in inspecting an air gap between two surfaces and, more particularly, to an inspection apparatus and control system for use with an inspection probe fixed to an extendable structure.

Machines, motors, and industrial equipment are generally inspected regularly to ensure proper function and operation, particularly long-life cycle equipment. Surfaces of turbine, boiler, and generator components, for example, are inspected for damage to prevent failure or damage during operation. In generators, for example, stator and rotor surfaces may be inspected via a narrow air gap defined between the stator and rotor using an inspection probe that is extended into the air gap without disassembling the generator, thus saving time, effort, and generator downtime for inspection.

For certain equipment, an inspection probe is fixed to an extendable structure that is guided into the air gap via a motor. In generators, for example, where the stator is ferromagnetic, the extendable structure includes one or more magnets that maintain contact with the stator via a magnetic adhesion as the inspection probe and extendable structure are extended into the air gap. The extendable structure provides support for the inspection probe as it is driven by the motor, extending into the air gap without bends or arches, and with a generally constant separation between the inspection probe and the stator. Certain structures, such as a steel band or tape, for example, are collected outside the air gap, in a roll for example. Extension and retraction of the steel band amounts to unrolling and rolling the steel band by the motor.

BRIEF DESCRIPTION

In one aspect, an inspection apparatus is provided. The inspection apparatus includes an extendable structure, an inspection probe, a drive, a sensor, and a processor. The extendable structure includes an end fixed to the inspection probe and insertable into a gap defined between a first surface and a second surface. The extendable structure is configured to maintain physical contact with the first surface as the end transitions across the first surface. The drive is configured to position the inspection probe. The sensor is coupled to the drive and configured to measure a drive load over a period of time the inspection probe transitions across the first surface. The processor is coupled to the sensor and is configured to receive a drive load signal associated with the drive load corresponding to movement of the inspection probe, and determine an operating condition of the extendable structure based on the drive load signal.

In another aspect, a control system for an inspection apparatus is provided. The control system includes a motor, a sensor, and a processor. The motor is configured to extend an extendable structure into a gap defined between a first surface and a second surface. The extendable structure includes an end insertable into the gap and couplable to an inspection probe. The extendable structure is configured to maintain physical contact with the first surface as the end transitions across the first surface. The sensor configured to measure a motor load over a period of time the inspection probe transitions across the first surface. The processor coupled to the sensor and configured to receive a motor load signal associated with the drive load corresponding to movement of the inspection probe, and determine an operating condition of the extendable structure based on the motor load signal.

DRAWINGS

These and other features, aspects, and advantages of the present disclosure will become better understood when the following detailed description is read with reference to the accompanying drawings in which like characters represent like parts throughout the drawings, wherein.

Figure 1:
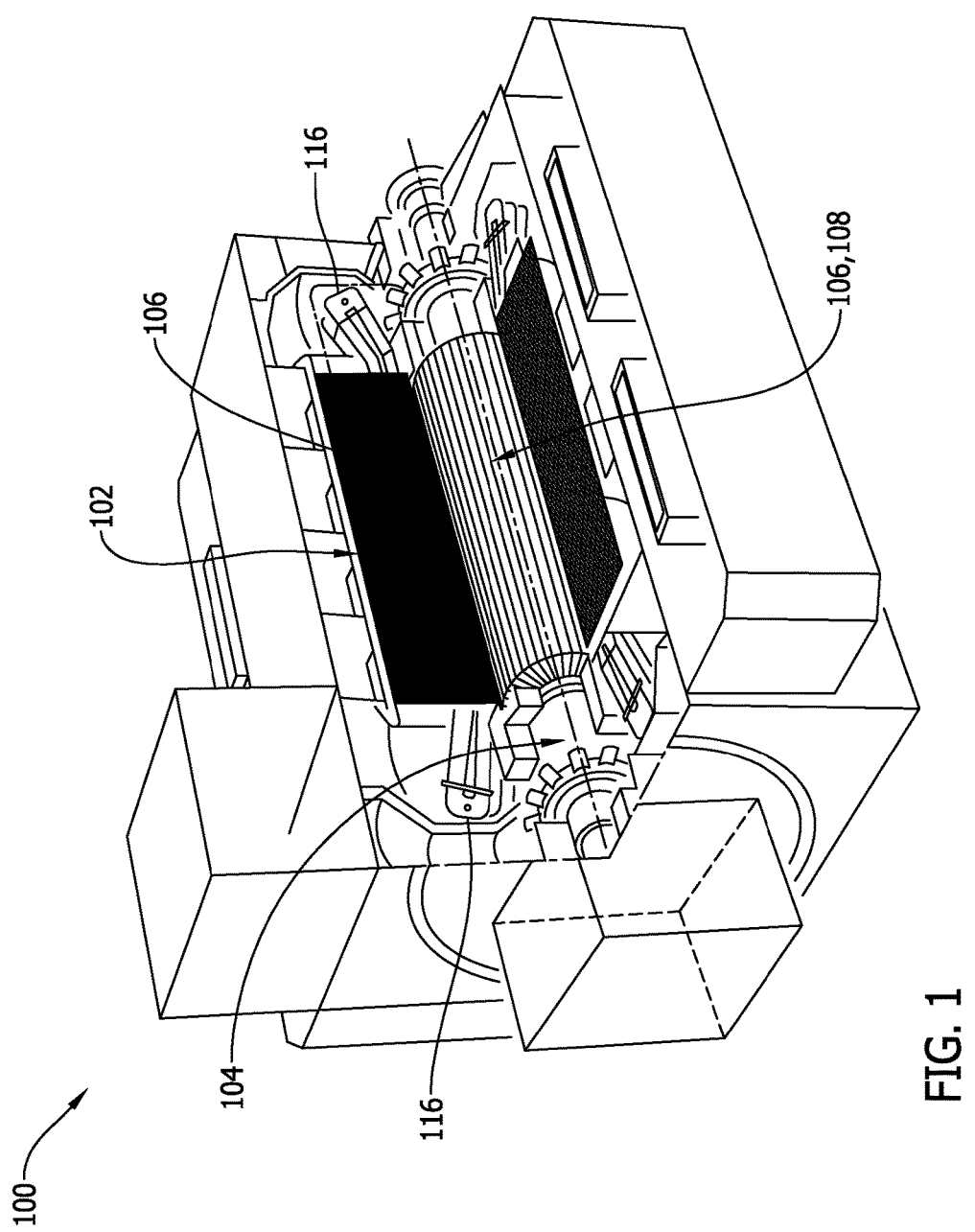
FIG. 1 is a perspective view of an exemplary generator for a power station.

Unless otherwise indicated, the drawings provided herein are meant to illustrate features of embodiments of this disclosure. These features are believed to be applicable in a wide variety of systems comprising one or more embodiments of this disclosure. As such, the drawings are not meant to include all conventional features known by those of ordinary skill in the art to be required for the practice of the embodiments disclosed herein.

DETAILED DESCRIPTION

In the following specification and the claims, a number of terms are referenced that have the following meanings. For example, the singular forms "a", "an", and "the" include plural references unless the context clearly dictates otherwise. Moreover, "optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

As used herein, the terms "processor" and "computer" and related terms, e.g., "processing device", "computing device", and "controller" are not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc—read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable, and include any computer program stored in memory for execution by personal computers, workstations, clients and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

Furthermore, as used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

Embodiments of the present disclosure relate to an inspection apparatus for a generator. The inspection apparatus described herein includes an inspection probe positionable within an air gap defined between a stator and rotor of a generator by an extendable structure driven by a drive, such as, for example, a motor. The inspection apparatus described herein facilitates monitoring operating conditions of the extendable structure as the inspection probe and extendable structure transition across a surface of the stator. More specifically, as the extendable structure slides along the surface of the stator, the inspection apparatus monitors the load on the drive to detect certain operating conditions of the extendable structure, including, for example, a blockage in the path of the extendable structure and inspection probe, and loss of magnetic adhesion between the extendable structure and the surface of the stator.

FIG. 1 is a perspective view of an exemplary generator 100 for use with a power station. Generator 100 includes a stator 102 and a rotor 104. Each of stator 102 and rotor 104 includes ferromagnetic elements 106 (white) and non-ferromagnetic elements 108 (grey).

Figure 2:
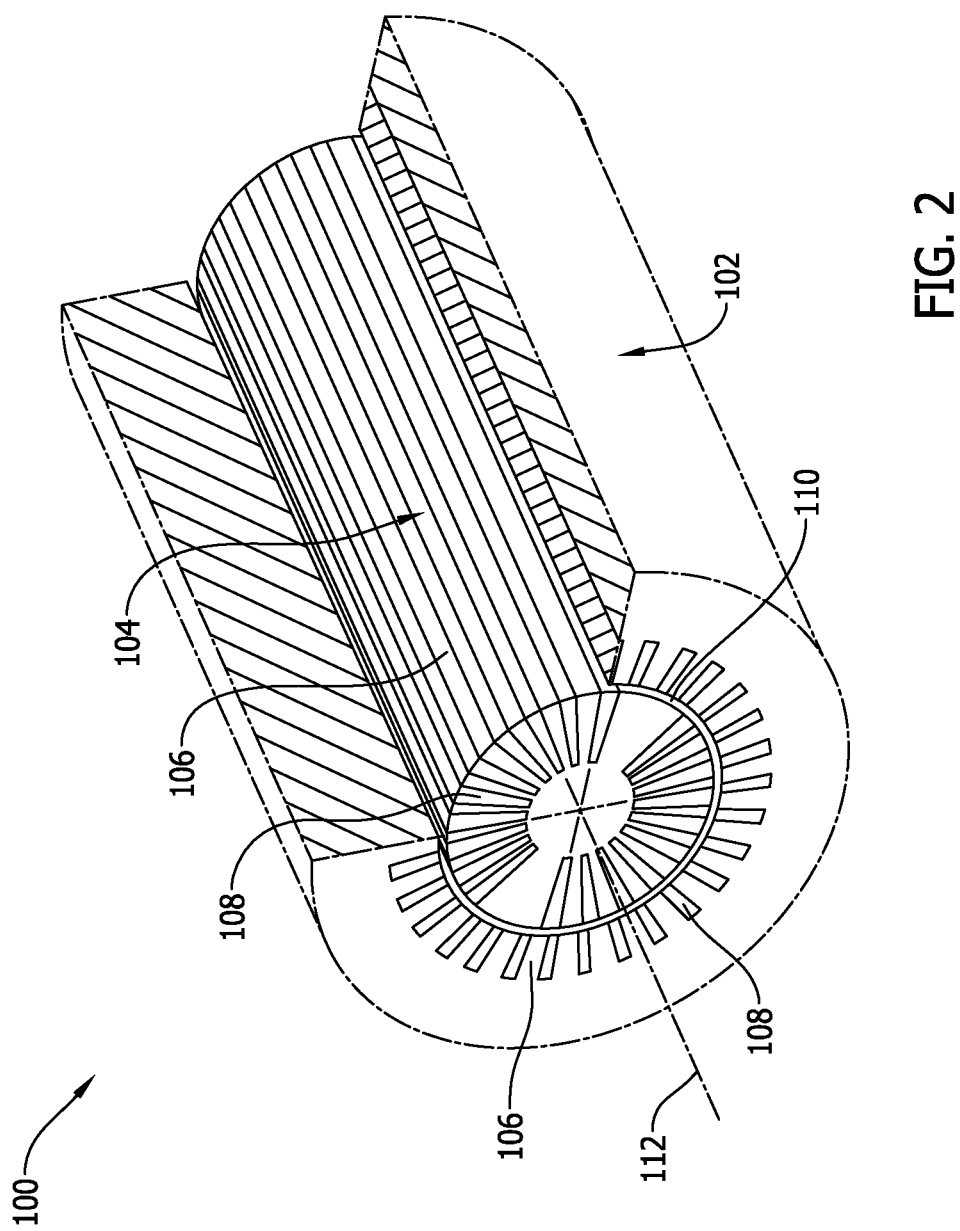
FIG. 2 is a detailed perspective view of an exemplary stator and a rotor used with the generator shown in FIG. 1.

FIG. 2 is a detailed perspective view of stator 102 and rotor 104 of generator 100 (shown in FIG. 1), including their respective ferromagnetic elements 106 and non-ferromagnetic elements 108. Stator 102 and rotor 104 are oriented such that a narrow, annular air gap 110 is defined there between. Ferromagnetic elements 106 and non-ferromagnetic elements 108 may be spaced in an alternating arrangement around the circumference of stator 102 and rotor 104, and extend substantively parallel to the generator axis 112.

Figure 3:
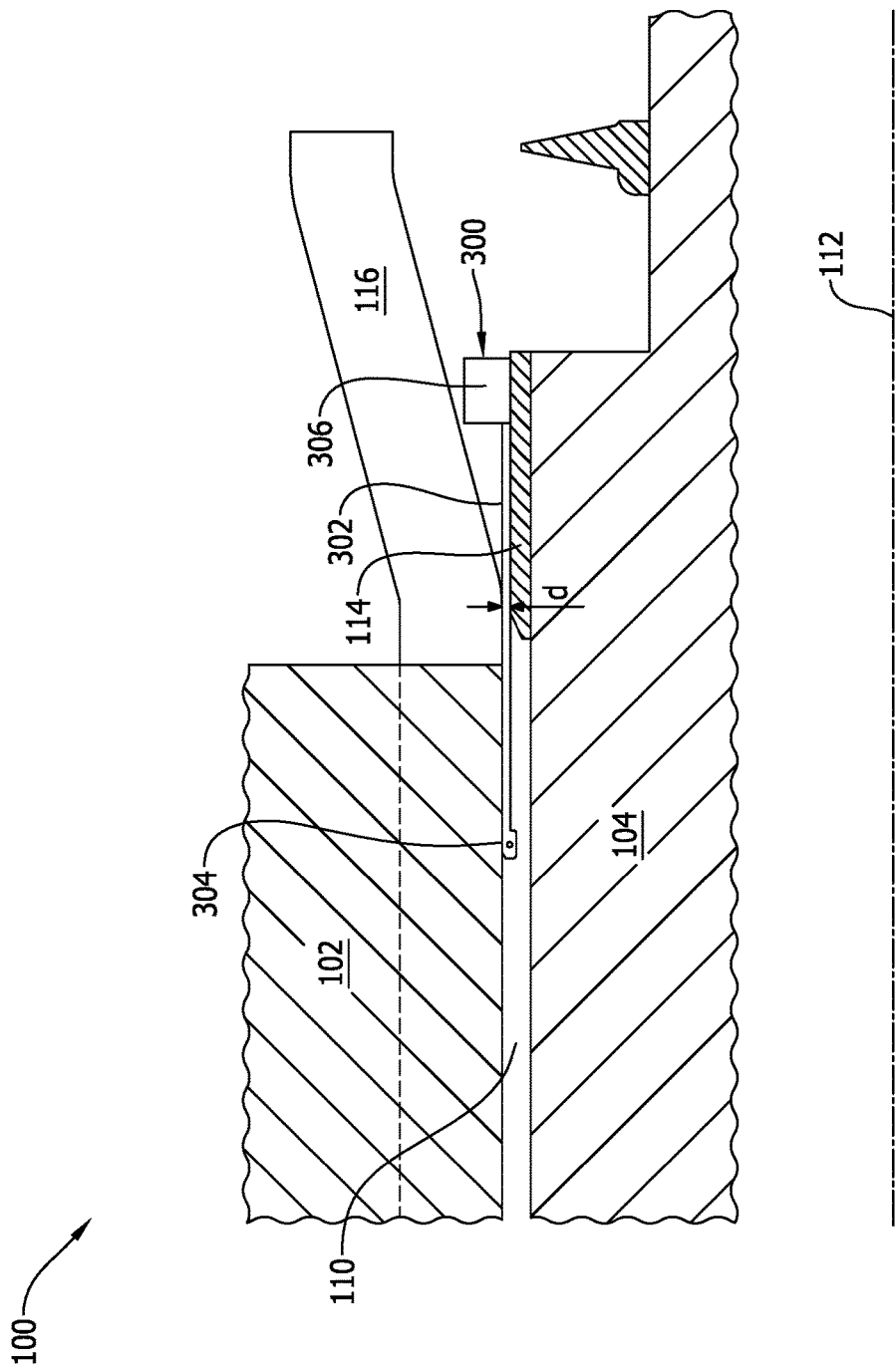
FIG. 3 is a cross sectional view of the generator shown in FIG. 1 and taken along line 3-3.

FIG. 3 is a cross-sectional view taken along line 3-3 and along generator axis 112 of generator 100, including air gap 110 defined by stator 102 and rotor 104 (shown in FIGS. 1 and 2). FIG. 3 also depicts an exemplary inspection apparatus 300, including an extendable structure 302 and an inspection probe 304 attached to an end thereof. Inspection apparatus 300 also includes a housing 306 for various components positioned external to air gap 110.

A rotor cap 114 is positioned on rotor 104 and extends substantively parallel to generator axis 112 and radially towards a stator bar 116. The stator bore and rotor cap 114 define a width d of air gap 110 into which extendable structure 302 and inspection probe 304 are insertable. In certain embodiments, width d is at least four millimeters (mm). Alternatively, inspection apparatus 300 and its components are variously arranged and sized to accept different shared geometries of generators. For example, in certain embodiments, inspection apparatus 300 includes a guide rail positioned between housing 306 and air gap 110 to facilitate guiding extendable structure 302 to the ferromagnetic surfaces of stator 102 and rotor 104.

Figure 4:
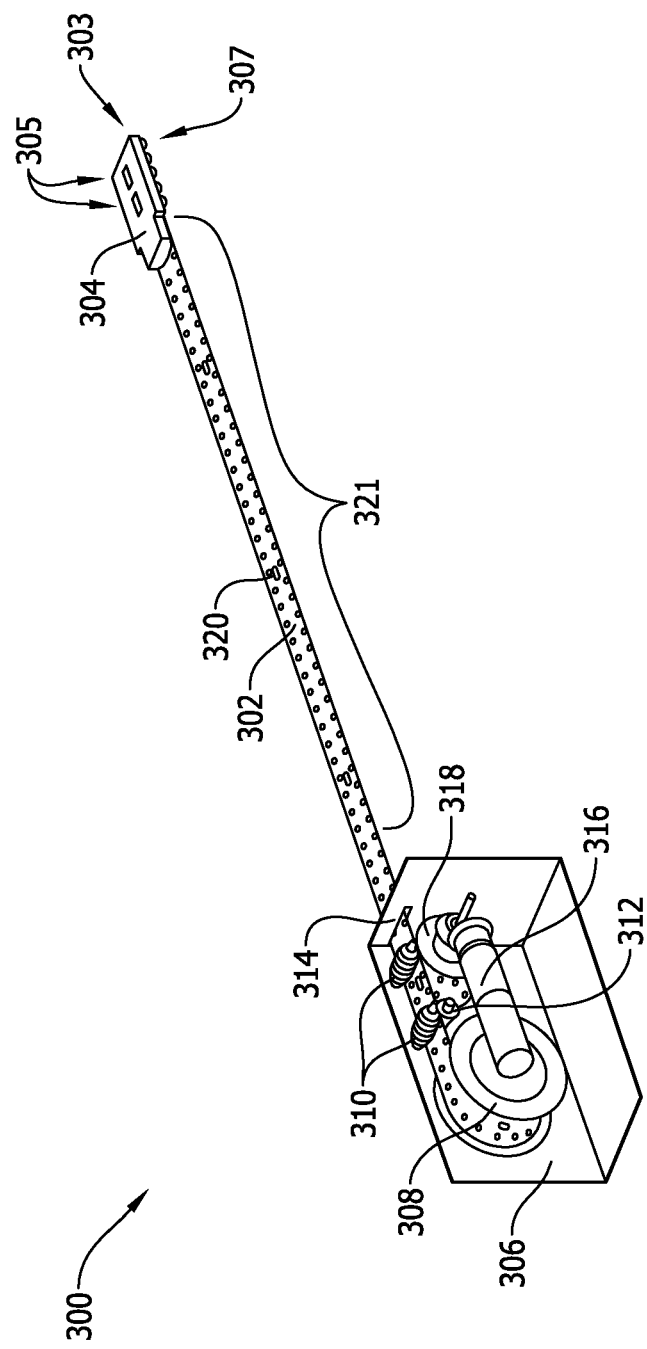
FIG. 4 is a block diagram of an exemplary inspection apparatus that may be used with the generator shown in FIGS. 1-3.

FIG. 4 is a detailed diagram of inspection apparatus 300. In the exemplary embodiment, inspection apparatus 300 includes extendable structure 302, inspection probe 304, and housing 306. Housing 306 contains a reel 308 on which extendable structure 302 is selectively rollable. When being extended, extendable structure 302 is unrolled from reel 308 and extruded through convex rollers 310, a concave roller 312, and an opening 314 defined in housing 306. When being retracted, extendable structure 302 is wound onto reel 308 for storage.

Extendable structure 302 includes an end 303 to which an inspection probe 304 is securely coupled. Inspection probe 304 includes, for example, one or more sensors 305 for inspection of surfaces, such as the surfaces of stator 102 and rotor 104 of generator 100. Inspection probe 304 is sized for insertion into air gap 110 defined between stator 102 and rotor 104, and is selectively positioned at a specific inspection site via extendable structure 302. Sensors 305 may include, for example, a camera, an eddy-current sensor, and/or a low-induction sensor. Inspection probe 304, in certain embodiments, includes one or more magnets 307 that interact with the ferromagnetic surface such that physical contact is maintained between inspection probe 304 and the ferromagnetic surface. Likewise, extendable structure 302 maintains physical contact with the ferromagnetic surface as its end 303 and inspection probe 304 transition across.

Inspection apparatus 300 includes a drive 316 that selectively extends and retracts extendable structure 302 to position inspection probe 304 within air gap 110. drive 316 is drivably coupled to reel 308 through a transport roller 318 and extendable structure 302. Drive 316 may include, for example, and without limitation, an electric or gas motor, a hydraulic motor, or a pneumatic motor. For example, where drive 316 includes an electric motor, drive 316 drives transport roller 318 to cause extendable structure 302 to selectively extend from and retract onto reel 308.

Extendable structure 302 includes a plurality of magnets 320 that are distributed along a length 321 of extendable structure 302. Magnets 320 interact with the ferromagnetic surface to magnetically maintain physical contact with the ferromagnetic surface by imparting a magnetic force on extendable structure. Magnets 320 further interact with the ferromagnetic surface to provide circumferential control. Magnets 320 enable extendable structure 302 and inspection probe 304 to be selectively positioned along the ferromagnetic surface without extendable structure 302 becoming detached while it is extended or retracted due to gravity or other operating conditions, such as, for example, a blockage in a path of extendable structure 302 and inspection probe 304 as end 303 and inspection probe 304 transition across the ferromagnetic surface. Under such operating conditions of extendable structure 302, extendable structure may sag and eventually buckle, potentially causing damage to inspection apparatus 300, stator 102, or rotor 104.

Extendable structure 302 is fabricated from a flexible elastic material, such as steel, for example, that is suitable for rolling up and unrolling from reel 308. In certain embodiments, extendable structure 302 includes an extrudable steel band. The steel band is extruded between convex rollers 310 and concave roller 312, forming a concave surface of the steel band opposite a convex surface of the steel band. Magnets 320 are positioned on the concave surface of extendable structure 302. The convex surface of extendable structure 302 faces the ferromagnetic surface causing the convex surface to slide along the ferromagnetic surface and to maintain physical contact with it. As the extrudable steel band is retracted, it is rolled onto reel 308.

Figure 5:
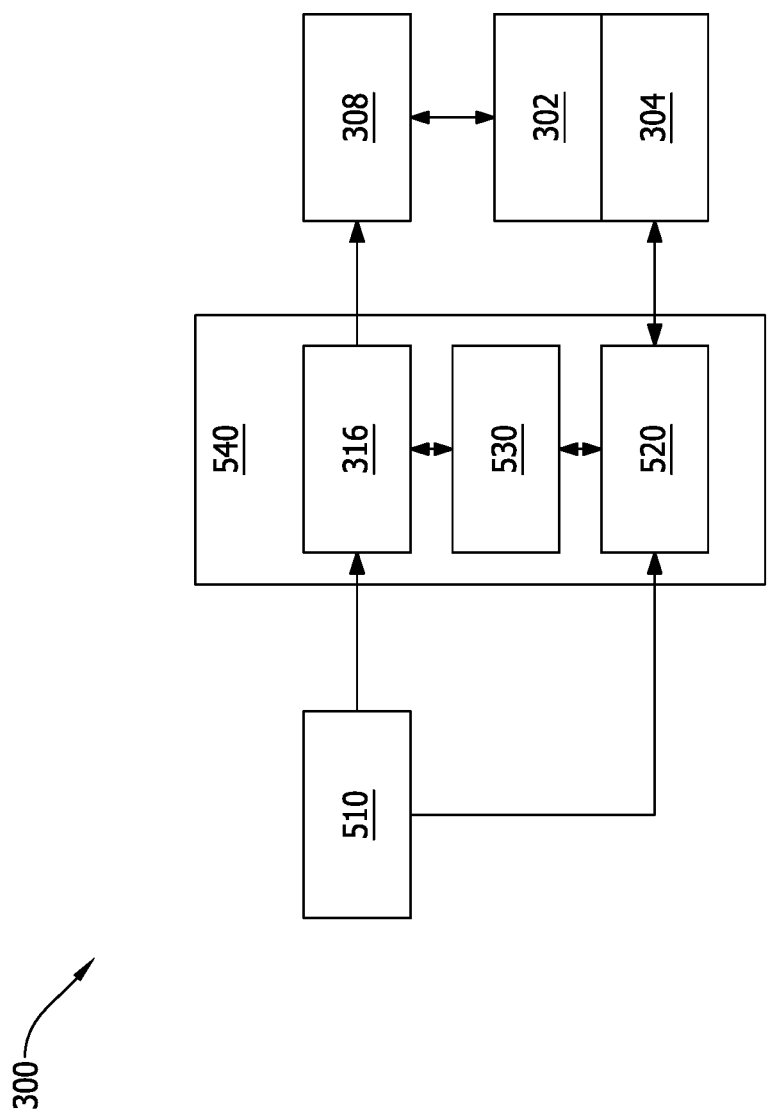
FIG. 5 is a block diagram of the inspection apparatus shown in FIG. 4.

FIG. 5 is a block diagram of an exemplary inspection apparatus 300 for use with generator 100 (shown in FIGS. 1-3). In the exemplary embodiment, inspection apparatus 300 includes a power supply 510 that provides power to drive 316. Drive 316 is drivably coupled to reel 308. Inspection apparatus 300 includes extendable structure 302 that is rolled onto reel 308 for storage and unrolled from reel 308 when extended to position inspection probe 304.

In the exemplary embodiment, inspection apparatus 300 includes a processor 520 and a sensor 530. Sensor 530 is coupled to drive 316 to measure a drive load during operation. For example, where drive 316 includes an electric motor, sensor 530 measure motor current during a period of time when extendable structure 302 is extended across the ferromagnetic surface of stator 102 or rotor 104, i.e., when end 303 and inspection probe 304 are transitioned across the ferromagnetic surface. Sensor 530 generates a motor current signal indicative of the motor current for drive 316. Together, processor 520, sensor 530, and drive 316 make up a control system 540 for inspection apparatus 300. In alternative embodiments, sensor 530 includes a current sensor coupled to power supply 510 to measure the motor current. In other embodiments, current sensor 530 is substituted for a motor torque sensor.

Processor 520 is coupled to sensor 530 to receive the drive load signal. Processor 520 monitors the drive load and determines the operating condition of extendable structure 302 based on the drive load.

In certain embodiments, processor 520 detects a drive load pattern indicative of the operating condition of extendable structure 302. For example, in embodiments utilizing an electric motor and current sensor, processor 520 computes average current based on the motor current signal, and detects "outlier" current measurements that correspond to sharp increases or decreases in motor current. The operating condition of extendable structure 302 may include, for example, a loss of magnetic adhesion, resulting in a loss of physical contact between extendable structure 302 and the ferromagnetic surface. Such a loss of physical contact would reduce the load, or torque, on drive 316, resulting in a drive load pattern indicating a decrease in the drive load corresponding to the decreased motor torque. The operating condition of extendable structure 302 may include for example, a blockage in a path of inspection probe 304 and extendable structure 302. Such a blockage would increase the load, or torque, on motor 316, resulting in a drive load pattern indicating an increase in the drive load corresponding to the increased drive torque. The operating condition of extendable structure 302 may further include circumferential drift of inspection probe 304 and extendable structure 302. Such circumferential drift may result, in certain circumstances, in reduced magnetic adhesion.

In certain embodiments, processor 520 suspends operation of drive 316 based on the determined operating condition of extendable structure 302. For example, if a blockage is encountered by extendable structure 302 and inspection probe 304, and a corresponding drive load pattern is detected, processor 520 suspends operation of drive 316 to prevent damage to inspection apparatus 300, stator 102, or rotor 104.

Figure 6:
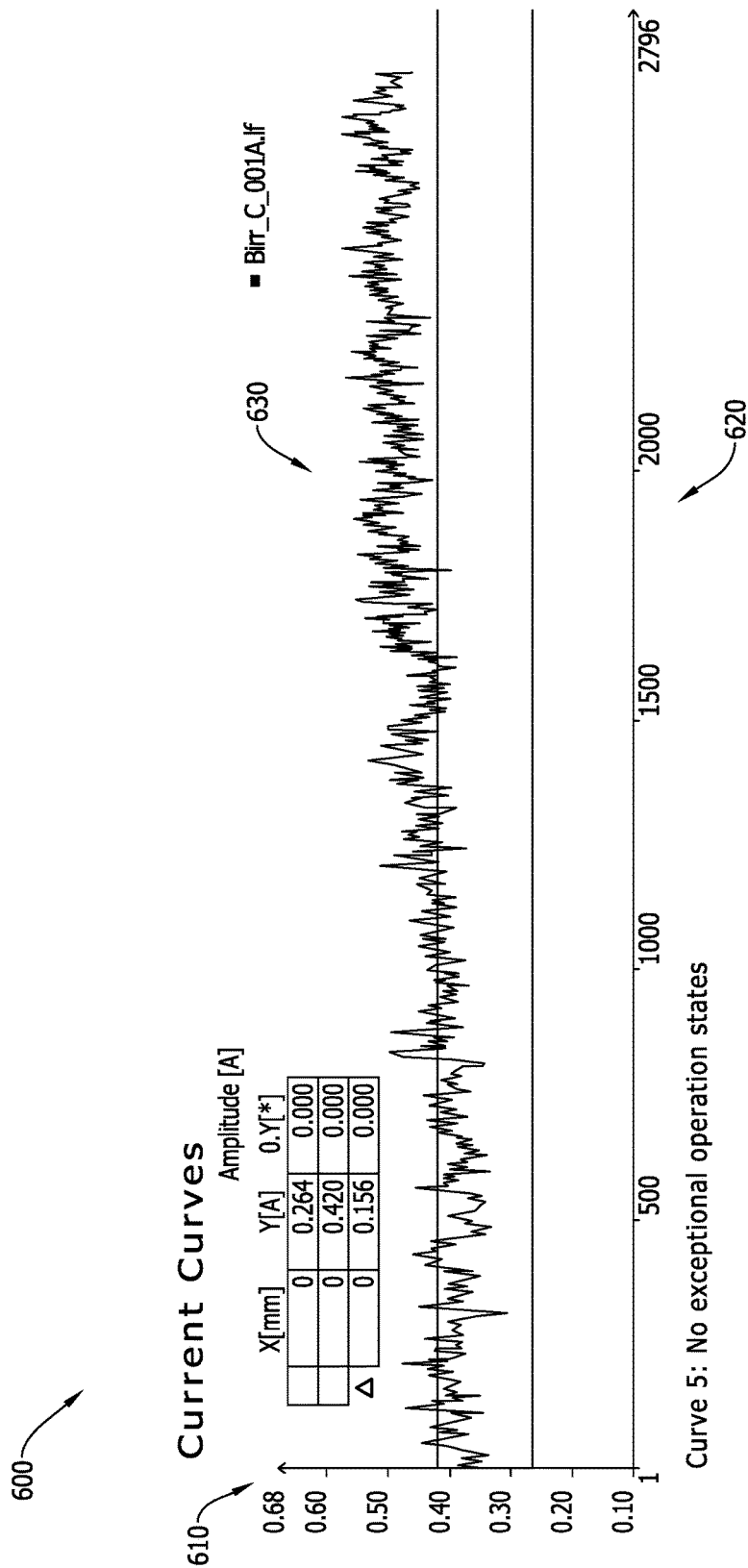
FIG. 6 is a motor current plot illustrating exemplary normal operating conditions for the extendable structure shown in FIGS. 3 and 4.

FIG. 6 is a motor current plot 600 illustrating exemplary normal operating conditions for extendable structure 302 (shown in FIGS. 3 and 4). Motor current plot 600 includes a vertical axis 610 representing motor current in Amperes (A). Vertical axis 610 illustrates a range from about 0 A to just over about 0.60 A. Motor current plot 600 includes a horizontal axis 620 representing an extension of extendable structure 302 into the air gap 110 defined by stator 102 and rotor 104 of generator 100 (shown in FIGS. 1-3). Extension of extendable structure 302 into air gap 110 is shown in mm, ranging from about 1 mm to about 2700 mm.

Motor current plot 600 illustrates a motor current signal 630 monitored over a period of time during which extendable structure 302 is extended by motor 316 (shown in FIGS. 4 and 5) from about 1 mm up to roughly about 2700 mm. Motor current signal 630 illustrates exemplary normal operating conditions for extendable structure 302, where motor current increases on average slowly as extendable structure 302 slides across the ferromagnetic surface. The slowly increasing motor current pattern indicates an accumulation of friction forces and magnetic forces imparted onto extendable structure 302. Processor 520 detects this motor current pattern and the corresponding normal operating conditions for extendable structure 302. The increase in motor current while extending extendable structure 302 is generally proportional to the motor torque demanded from motor 316. Motor 316 is drivably coupled to reel 308 through transit roller 318 for selectively extending and retracting extendable structure 302. When extending extendable structure 302, motor 316 drives transit roller 318, and therefore reel 308, with a motor torque increasing proportionally to a surface area of extendable structure 302 in physical contact with the ferromagnetic surface.

Figure 7:
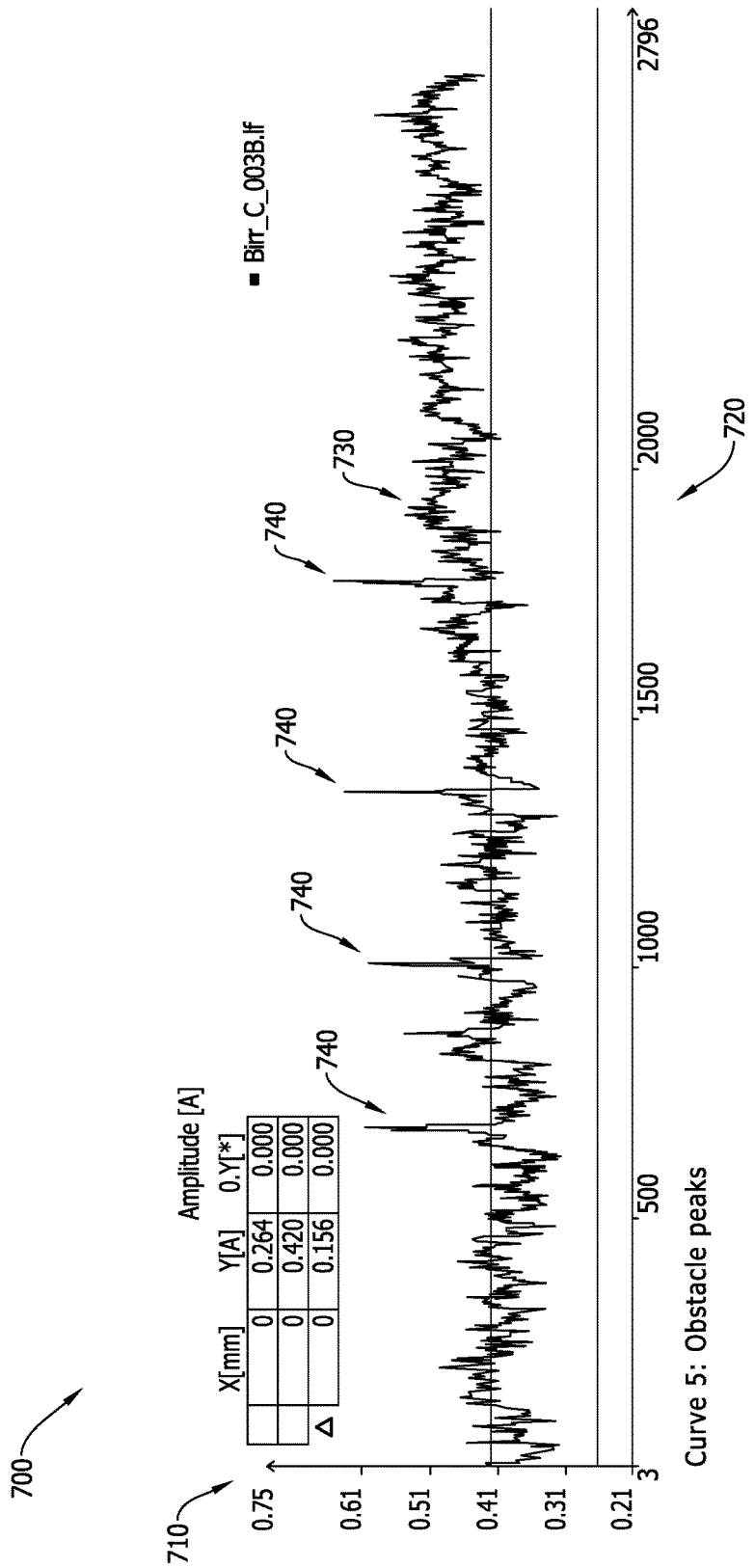
FIG. 7 is a motor current plot illustrating exemplary normal operating conditions for the extendable structure shown in FIGS. 3 and 4 with multiple obstacles.

FIG. 7 is a motor current plot 700 illustrating normal operating conditions for extendable structure 302 (shown in FIGS. 3 and 4) with multiple obstacles. Motor current plot 700 includes a vertical axis 710 representing motor current in Amperes (A). Vertical axis 710 illustrates a range from 0.21 A to 0.75 A. Motor current plot 700 includes a horizontal axis 720 representing extension of extendable structure 302 into air gap 110 defined by stator 102 and rotor 104 of generator 100 (shown in FIGS. 1-3). Extension of extendable structure 302 into air gap 110 is shown in mm, ranging from 3 mm to over 2700 mm.

Motor current plot 700 illustrates a motor current signal 730 monitored over a period of time during which extendable structure 302 is extended by motor 316 (shown in FIGS. 4 and 5) from 3 mm up to roughly 2700 mm. Motor current signal 730 illustrates normal operating conditions for extendable structure 302, where motor current increases on average slowly as extendable structure 302 slides across the ferromagnetic surface. Motor current signal 730 further illustrates occurrences of obstacles indicated by sharp motor current spikes 740. The obstacles occur at about 700 mm, 1000 mm, 1350 mm, and 1750 mm extension of extendable structure 302. Current spikes 740 correspond to increases in motor torque to overcome the obstacles.

Figure 8:
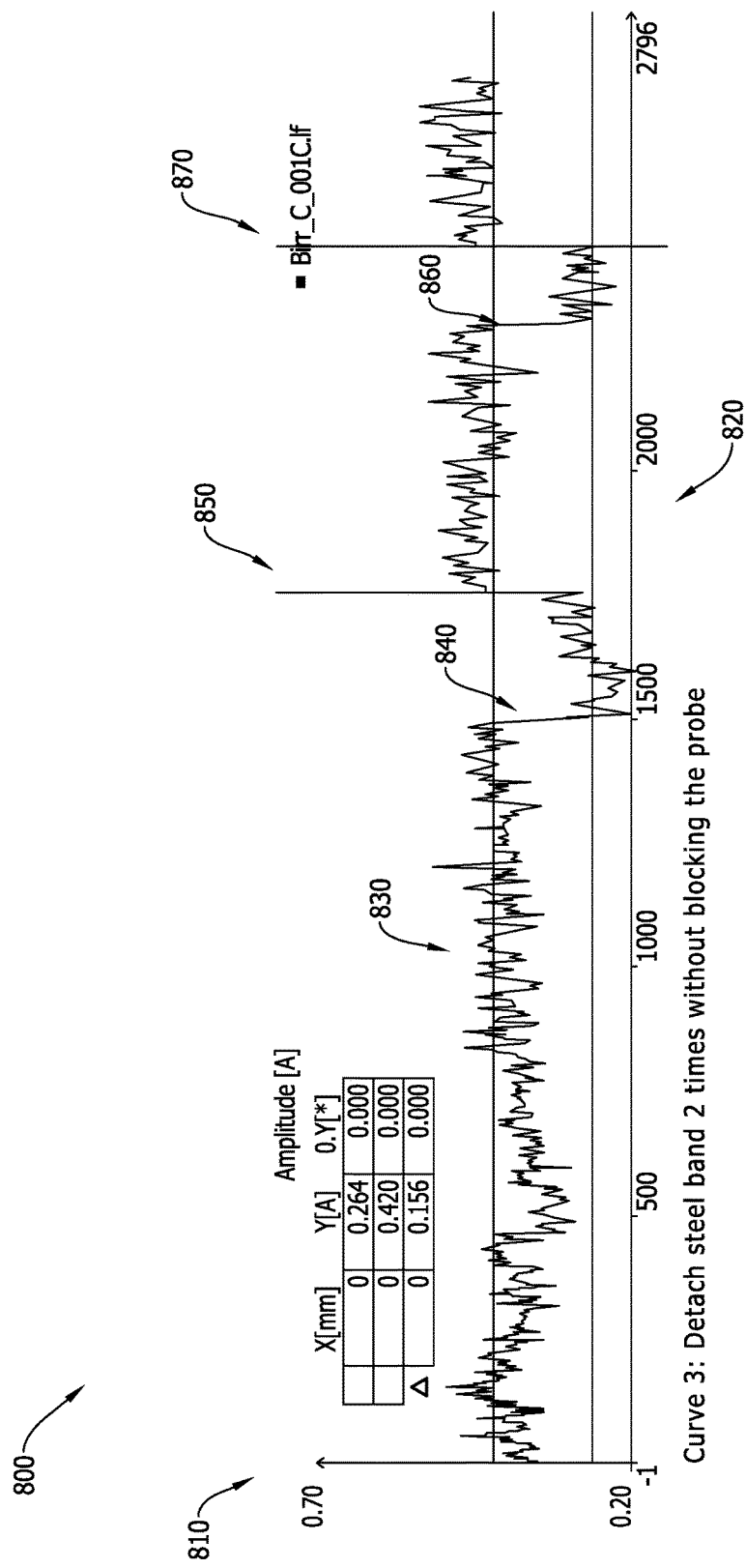
FIG. 8 is a motor current plot illustrating exemplary loss of physical contact between the extendable structure and ferromagnetic surface shown in FIGS. 3 and 4.

FIG. 8 is a motor current plot 800 illustrating a loss of physical contact between extendable structure 302 and the ferromagnetic surface of stator 102 or rotor 104 (shown in FIGS. 1-4). Motor current plot 800 includes a vertical axis 810 representing motor current in Amperes (A). Vertical axis 810 illustrates a range from 0.20 A to 0.70 A. Motor current plot 800 includes a horizontal axis 820 representing extension of extendable structure 302 into air gap 110 defined by stator 102 and rotor 104 of generator 100 (shown in FIGS. 1-3). Extension of extendable structure 302 into air gap 110 is shown in mm, ranging from −1 mm to over 2700 mm.

Motor current plot 800 illustrates a motor current signal 830 monitored over a period of time during which extendable structure 302 is extended by motor 316 (shown in FIGS. 4 and 5) from −1 mm up to roughly 2700 mm. Motor current signal 830 illustrates normal operating conditions for extendable structure 302, where motor current increases on average slowly as extendable structure 302 slides across the ferromagnetic surface until about 1500 mm extension. At about 1500 mm extension, motor current signal 830 illustrates a sharp decrease 840 in motor current, indicating a loss of physical contact between extendable structure 302 and the ferromagnetic surface. Under such an operating condition, the magnetic adhesion of extendable structure 302 is dramatically reduced as the length of extendable structure 302 separates from the ferromagnetic surface and fewer of magnets 320 interact with the ferromagnetic surface, thus demanding less motor torque to drive extendable structure.

Motor current signal 830 further illustrates a sharp increase 850 in motor current at about 1750 mm extension, indicating physical contact is reestablished between extendable structure 302 and the ferromagnetic surface. The motor current pattern is repeated again between around 2300 mm and 2500 mm with a sharp decrease 860 and a sharp increase 870.

Figure 9:
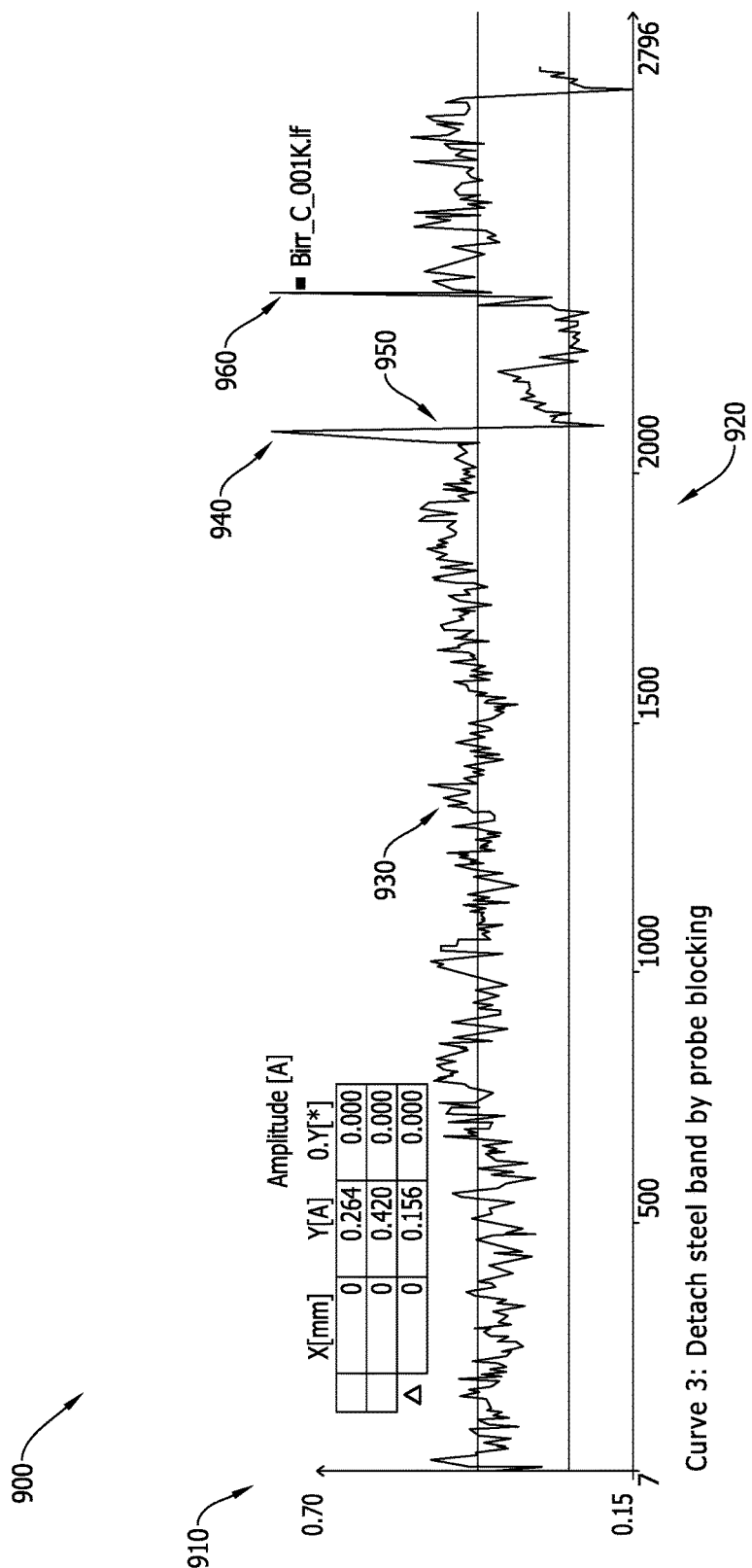
FIG. 9 is a motor current plot illustrating exemplary blockage of the extendable structure shown in FIGS. 3 and 4.

FIG. 9 is a motor current plot 900 illustrating a blockage of extendable structure 302 and inspection probe 304 along their path across the ferromagnetic surface of stator 102 or rotor 104 (shown in FIGS. 1-4). Motor current plot 900 includes a vertical axis 910 representing motor current in Amperes (A). Vertical axis 910 illustrates a range from 0.15 A to 0.70 A. Motor current plot 900 includes a horizontal axis 920 representing extension of extendable structure 302 into air gap 110 defined by stator 102 and rotor 104 of generator 100 (shown in FIGS. 1-3). Extension of extendable structure 302 into air gap 110 is shown in mm, ranging from 7 mm to over 2700 mm.

Motor current plot 900 illustrates a motor current signal 930 monitored over a period of time during which extendable structure 302 is extended by motor 316 (shown in FIGS. 4 and 5) from 7 mm up to roughly 2700 mm. Motor current signal 930 illustrates normal operating conditions for extendable structure 302, where motor current increases on average slowly as extendable structure 302 slides across the ferromagnetic surface until about 2100 mm extension. At about 2100 mm extension, motor current signal 930 illustrates a sharp increase 940 in motor current, indicating a blockage in the path of inspection probe 304 and extendable structure 302. Under such an operating condition, motor torque increases sharply to overcome the blockage, ultimately resulting in loss of physical contact between extendable structure 302 and the ferromagnetic surface as extendable structure 302 sags or buckles. The sharp increase 940 in motor current is followed by a sharp decrease 950 in motor current as extendable structure 302 separates from the ferromagnetic surface and fewer of magnets 320 interact with the ferromagnetic surface, thus demanding less motor torque to drive extendable structure. The motor current pattern of sharp increase 940 and sharp decrease 950 is followed by a sharp increase 960 in motor current when the blockage is overcome and physical contact is reestablished between extendable structure 302 and the ferromagnetic surface.

The above described inspection apparatus includes an inspection probe positionable within an air gap defined between a stator and rotor of a generator by an extendable structure driven by a motor. The inspection apparatus described herein facilitates monitoring operating conditions of the extendable structure as the inspection probe and extendable structure transition across a surface of the stator. More specifically, as the extendable structure slides along the surface of the stator, the inspection apparatus monitors current to the motor to detect certain operating conditions of the extendable structure, including, for example, a blockage in the path of the extendable structure and inspection probe, and loss of magnetic adhesion between the extendable structure and the surface of the stator.

An exemplary technical effect of the methods, systems, and apparatus described herein includes at least one of: (a) monitoring motor current to detect operating conditions of an extendable structure as it slides across a stator or rotor surface to position an inspection probe within an air gap, (b) detecting motor current patterns indicative of various abnormal operating conditions of the extendable structure, including, for example, blockages and loss of magnetic adhesion and physical contact with the rotor or stator, (c) detecting blockages and loss of magnetic adhesion and physical contact in real-time, (d) controlling extension and retraction of the extendable structure based on operating conditions thereof determined in real-time, (e) reducing damage and failures of air gap inspection apparatus, generator stator, and generator rotor through early detection of abnormal operating conditions for the extendable structure, and (f) improving lifecycle costs of generators through reduced damage to stator and rotor during inspections due to blockages or loss of magnetic adhesion of the extendable structure.

Exemplary embodiments of methods, systems, and apparatus for rod pumping unit controllers are not limited to the specific embodiments described herein, but rather, components of systems and/or steps of the methods may be utilized independently and separately from other components and/or steps described herein. For example, the methods may also be used in combination with other non-conventional air gap inspection probe, and are not limited to practice with only the systems and methods as described herein. Rather, the exemplary embodiment can be implemented and utilized in connection with many other applications, equipment, and systems that may benefit from reduced cost, reduced complexity, commercial availability, improved reliability at high temperatures, and increased memory capacity.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An inspection apparatus, comprising:
    an extendable structure comprising an end insertable into a gap defined between a first surface and a second surface, said extendable structure configured to maintain physical contact with the first surface as said end transitions across the first surface;
    an inspection probe fixed to said end of said extendable structure and positionable within the gap by a drive;
    a sensor configured to measure a drive load over a period of time during which said end and said inspection probe transitions across the first surface; and
    a processor coupled to said sensor and configured to:
        receive a signal associated with the drive load corresponding to movement of said inspection probe, and determine an operating condition of said extendable structure based on the signal.

2. The inspection apparatus of claim 1, wherein the first surface is a ferromagnetic surface, and wherein said extendable structure further comprises a plurality of magnets distributed along said extendable structure, said plurality of magnets configured to interact with the ferromagnetic surface to magnetically maintain physical contact with the first surface as said end transitions across the first surface, and magnetically guide said end circumferentially.

3. The inspection apparatus of claim 1, wherein the extendable structure comprises an extrudable steel band comprising a concave surface opposite a convex surface, said convex surface configured to contact the first surface.

4. The inspection apparatus of claim 1, wherein said processor is further configured to detect a drive load pattern indicative of the operating condition of said extendable structure, the operating condition comprising a blockage in a path of said inspection probe, the drive load pattern including an increase in the drive load corresponding to an increased drive torque.

5. The inspection apparatus of claim 1, wherein said processor is further configured to detect a drive load pattern indicative of the operating condition of said extendable structure, the operating condition comprising a loss of physical contact between said extendable structure and the first surface, the drive load pattern including a decrease in the drive load corresponding to a decreased drive torque.

6. The inspection apparatus of claim 1, wherein said processor is further configured to suspend operation of said drive based on the operating condition of said extendable structure.

7. The inspection apparatus of claim 1, wherein the first surface is a ferromagnetic surface, and wherein said inspection probe comprises:
    a sensor configured to inspect at least one of the ferromagnetic surface and the second surface; and
    a magnet configured to magnetically couple to the ferromagnetic surface such that said extendable structure is maintained in contact with the ferromagnetic surface as said inspection probe and said end of said extendable structure transition across the ferromagnetic surface.

8. The inspection apparatus of claim 1 further comprising a reel, wherein said drive is drivably coupled to said reel for selectably extending and retracting said extendable structure relative to said reel.

9. A control system for an inspection apparatus, said control system comprising:
    a motor configured to extend an extendable structure into a gap defined between a first surface and a second surface, said extendable structure comprising an end insertable into the gap and couplable to an inspection probe, said extendable structure configured to maintain physical contact with the first surface as said end transitions across the first surface;
    a sensor configured to measure a motor load over a period of time said inspection probe transition across the first surface;
    a processor coupled to said sensor and configured to:
        receive a signal associated with the motor load corresponding to movement of said inspection probe, and determine an operating condition of the extendable structure based on the signal.

10. The control system of claim 9, wherein said processor is further configured to detect a motor load pattern indicative of the operating condition of said extendable structure, the operating condition comprising a blockage in a path of said inspection probe, the motor load pattern including an increase in the motor load corresponding to an increased motor torque.

11. The control system of claim 9, wherein said processor is further configured to detect a motor load pattern indicative of the operating condition of the extendable structure, the operating condition comprising a loss of physical contact between said extendable structure and the first surface, the motor load pattern including a decrease in the motor load corresponding to a decreased motor torque.

12. The control system of claim 9, wherein said processor is further configured to suspend operation of said motor based on the operating condition of said extendable structure.

13. The control system of claim 9, wherein said motor is drivably coupled to a reel for selectably extending and retracting said extendable structure, said motor further configured, when extending said extendable structure, to drive said reel with a motor torque increasing proportionally to a surface area of said extendable structure in physical contact with the first surface.

14. The control system of claim 9, wherein said processor is further configured to detect a motor load pattern indicative of the operating condition of said extendable structure, the operating condition comprising normal extension of said extendable structure with contact with the first surface, the motor load pattern including an increase in motor current corresponding to a proportional increase in motor torque.

15. The control system of claim 14, wherein the first surface is a ferromagnetic surface, and wherein said extendable structure further comprises a plurality of magnets distributed along the extendable structure, said plurality of magnets configured to interact with the ferromagnetic surface to magnetically maintain physical contact with the first surface as the end transitions across the first surface, and wherein said processor is further configured to detect a second motor load pattern indicative of an accumulative magnetic force imparted by the plurality of magnets onto said extendable structure.

* * * * *